United States Patent [19]

Tabak

[11] 4,254,295

[45] Mar. 3, 1981

[54] OLIGOMERIZATION OF OLEFINS

[75] Inventor: Samuel A. Tabak, Wenonah, N.J.

[73] Assignee: Mobil Oil Corporation, New York, N.Y.

[21] Appl. No.: 100,591

[22] Filed: Dec. 5, 1979

[51] Int. Cl.$^3$ .............................................. C07C 2/02
[52] U.S. Cl. .................................... 585/533; 585/510
[58] Field of Search ................................ 585/533, 510

[56] References Cited

U.S. PATENT DOCUMENTS 4,021,502   5/1977   Plank et al. ........................... 585/533

Primary Examiner—Curtis R. Davis
Attorney, Agent, or Firm—Charles A. Huggett

[57] ABSTRACT

A process for the selective oligomerization of linear and branched chain $C_2$ to $C_{12}$ olefins is provided. The process comprises contacting of the said olefin in the liquid phase with ZSM-12 at temperatures of 80° F. to 400° F.

10 Claims, No Drawings

OLIGOMERIZATION OF OLEFINS

BACKGROUND OF THE INVENTION

1. Field of the Invention

The invention relates to a method for oligomerizing straight and branched chain olefins having from 2 to about 12 carbon atoms by passing such olefins over a ZSM-12 zeolite.

2. Description of the Prior Art

It has long been known to contact various hydrocarbon fractions with acidic catalysts generally and, in particular, with solid siliceous acidic catalysts—including those referred to as crystalline aluminosilicate zeolites. Contact of hydrocarbon feeds with such acid catalysts is carried out for a wide variety of reactions, including cracking, isomerization, hydrocracking, etc. Representative U.S. patents disclosing and claiming contacting various hydrocarbon fractions with crystalline aluminosilicates are U.S. Pat. Nos. 3,140,249; 3,140,251; 3,140,253; and 3,140,322.

Oligomerization and polymerization of olefins in the gas phase over various zeolites such as Linde A, X and Y is also known to the art. A major problem associated with such reactions is the formation of very high boiling hydrocarbons which remain on the catalyst and block the active sites. This causes rapid aging of the catalysts.

Conversion of $C_2$ to $C_5$ olefins over ZSM-5 catalysts is also known to the art. In U.S. Pat. No. 3,960,978, a process for producing a gasoline fraction containing predominately olefinic compounds which comprises contacting $C_2$ to $C_5$ olefins with a ZSM-5 type crystalline aluminosilicate zeolite at a temperature of from about 500° F. to about 900° F. is disclosed. In U.S. Pat. No. 3,827,968, a two step process comprising oligomerization of a gaseous $C_2$ to $C_5$ olefin containing stream by contacting with a ZSM-5 type of zeolite at a temperature of from about 550° F. to 850° F. followed by aromatization of the product of the oligomerization reaction is disclosed. The processes disclosed in these patents differ from that of the present invention in that they employ a different catalyst and higher temperatures.

Zeolite ZSM-12 and hydrocarbon conversion over ZSM-12 are disclosed in U.S. Pat. No. 3,832,449 and U.S. Pat. No. 3,970,544 respectively. In U.S. Pat. No. 3,775,501, a process for the production of aromatics which comprises passing a mixture of air or oxygen and a hydrocarbon having from 2 to about 16 carbon atoms over a ZSM-12 zeolite at a temperature between about 500° F. and 1300° F. is disclosed. These patents do not disclose the oligomerization process of the present invention.

In U.S. Pat. No. 4,021,502, a process is disclosed in which gaseous $C_2$ to $C_5$ olefins are converted into gasoline blending stock by passage over ZSM-12 at temperatures of from about 450° F. to about 1200° F. The process disclosed in this patent differs from that of the present invention in that the process of the present invention utilizes temperatures much lower than those disclosed in the patent.

SUMMARY OF THE INVENTION

In accordance with the present invention, there has been discovered a process for the selective oligomerization of linear and branched chain $C_2$ to $C_{12}$ olefins which process comprises contacting such olefins, in the liquid phase, with a ZSM-12 zeolite at temperatures from about 80° F. to about 400° F.

It has been found that the present process provides selective conversion of the olefin feed to oligomer products. In other words, the present process effects the conversion of the olefin feed to dimer, trimer, tetramer, etc., products with high selectivity. The product of the present reaction thus contains primarily olefin oligomer and little or no light cracked products, paraffins, etc. While not wishing to be bound by any theory, it is believed that this desirable result is brought about by contacting the olefin feed with the ZSM-12 zeolite at low temperatures of from about 80° F. to about 400° F. The low temperature operation allows the oligomerization reaction to proceed but does not favor undesirable side reactions such as cracking.

A significant feature of the present process is the liquid phase contacting of the olefin feed and the ZSM-12 zeolite. Again, while not wishing to be bound by any theory, it is believed that contacting the olefin feed and ZSM-12 zeolite in the liquid phase results in substantially increased catalyst life. This is because operation in the liquid phase tends to "wash" higher boiling products from the surface of the ZSM-12, thus preventing the build-up of such products and the concomitant blocking of active sites. By way of comparison, if the reaction were run in the gas phase, the higher boiling products would tend to deposit on the surfaces of the ZSM-12 catalyst and cause severe aging by blocking the active sites.

In accordance with the present invention, straight and branched chain olefins having from 2 to 12 carbon atoms, preferably from 2 to about 6 carbon atoms, are contacted with a catalyst comprising a ZSM-12 zeolite, in the liquid phase, at temperatures of from about 80° to about 400° F. and a WHSV, based on zeolite, of from about 0.1 to about 5. Preferred are temperatures of from 100° to about 300° F. It will be appreciated that the pressures employed must be sufficient to maintain the system in the liquid phase. As is known to the art, the pressure will be a function of the number of carbon atoms of the feed olefin and the temperature. Suitable pressures include from about 0 psig to about 3000 psig.

Olefins which are converted according to the process of the present invention include: All straight chain and branched chain olefins, and diolefins for example ethylene, propylene, butylene, pentene, hexene, octene and the like, and mixtures thereof.

The oligomerization process described herein may be carried out as a batch type, semicontinuous or continuous operation utilizing a fixed or moving bed catalyst system.

DESCRIPTION OF SPECIFIC EMBODIMENTS

ZSM-12 is described in U.S. Pat. No 3,832,449, the contents of which is incorporated by reference. Particularly, ZSM-12 has a composition, expressed as mole ratios of oxides, as follows:

$$1.0 \pm 0.4 M_{2/n}O \cdot W_2O_3 \cdot 20-100 YO_2 \cdot zH_2O$$

wherein M is a cation, n is the valence of said cation, W is selected from the group consisting of aluminum and gallium, Y is selected from the group consisting of silicon and germanium and z is from 0 to 60. In a preferred synthesized form M is selected from the group consisting of a mixture of alkali metal cations, especially sodium, and tetraalkylammonium cations, the alkyl groups preferably containing two to five carbon atoms. Alternately, the reaction mixture obtained from the mixing of an alkylamine and a n-alkylhalide or sulfate or other alkylating agent can be used in place of the tetraethylammonium cations. The term reaction mixture encompasses either the mixture of tertiary amine and alkylating agent or a mixture of the aforesaid tertiary amine and alkylating agent.

In a preferred embodiment of ZSM-12, W is aluminum, Y is silicon and the silica/alumina mole ratio is at least 20 and ranges up to about 100.

ZSM-12 zeolites possess a definite distinguising crystalline structure whose X-ray diffraction pattern shows the following significant lines:

TABLE 1

| Interplanar spacing D(A) | Relative Intensity |
|---|---|
| 11.9 ± 0.2 | M |
| 10.1 ± 0.2 | M |
| 4.76 ± 0.1 | W |
| 4.29 ± 0.08 | VS |
| 3.98 ± 0.08 | M |
| 3.87 ± 0.07 | VS |
| 3.49 ± 0.07 | W |
| 3.38 ± 0.07 | M |
| 3.20 ± 0.06 | W |
| 3.05 ± 0.05 | W |
| 2.54 ± 0.03 | W |

These values were determined by standard techniques.

Zeolites ZSM-12 can be suitably prepared by preparin a solution containing tetraethyl ammonium cations, sodium oxide, an oxide of aluminum or gallium, an oxide of silica or germanium, and water and having a composition, in terms of mole ratios of oxides, falling within the following ranges:

TABLE 2

| | Broad | Preferred | Particularly Preferred |
|---|---|---|---|
| $OH^-/YO_2$ | 0.10–0.40 | 0.15–0.25 | 0.17–0.20 |
| $R_4N+/(R_4N+ + Na+)$ | 0.2–0.95 | 0.28–0.90 | 0.3–0.5 |
| $H_2 7/8/OH^-$ | 20–300 | 5.0–100 | 80–100 |
| $YO_2/W_2O_3$ | 40–200 | 85–125 | 90–100 | wherein R is ethyl, W is aluminum or gallium and Y is silicon or germanium, and maintaining the mixture until crystals of the zeolite are formed. Thereafter, the crystals are separated from the liquid and recovered. Typical reaction conditions consist of heating the foregoing reaction mixture to a temperature of from about 80° C. to 180° C. for a period of time of from about 6 hours to 150 days. A more preferred temperature range is from about 150° C. to 170° C. with the amount of time at a temperature in such range being from about 5 days to 12 days.

ZSM-12 is preferentially synthesized form a mixture containing a high silica to alimina ratio for example more than 85 to 1, especially at crystallization temperatures of 212° F. At this temperature, if the silica to alumina ratio drops to 50, conditions favor the formation of beta zeolite.

When the reaction product of triethylamine and diethylsulfate is used in the synthesis of ZSM-12 temperatures of under 175° C. should be maintained. Higher temperatures favor the formation of other zeolites.

The digestion of the gel particles is carried out until crystals form. The solid product is separated from the reaction medium, as by cooling the whole to room temperature, filtering and water washing.

The foregoing product is dried, e.g., at 230° F. for from about 16 to 24 hours. Of couse, milder conditions may be employed if desired, e.g., room temperature under vacuum.

ZSM-12 is preferably formed as an aluminosilicate. The composition can be prepared utilizing materials which supply the appropriate oxide. Such compositions include for an aluminosilicate, sodium aluminate, alumina, sodium silicate, silica hydrosol, silica gel, silicic acid, sodium hydroxide and tetraethylammonium compounds, e.g., teraethylammonium bromide. It will be understood that each oxide component utilized in the reaction mixture for preparing a member of the ZSM-12 family can be supplied by one or more initial reactants and they can be mixed together in any order. For example, sodium oxide can be supplied by an aqueous solution of sodium hydroxide, or by an aqueous solution of sodium silicate, tetraethylammonium cation can be supplied by tetraethylammonium hydroxide, tetraethylammonium bromide or by a mixture of diethylsulfate and triethylamine. The reaction mixture can be prepared either batchwise or continuously. Crystal size and crystallization time of the ZSM-12 composition will vary with the nature of the reaction mixture employed.

ZSM-12 zeolites can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel.

Typical ion exchange techniques would be to contact the ZSM-12 zeolites with a salt of the desired replacing cation or cations. Although a wide variety of salts can be employed, particular preference is given to chlorides, nitrates and sulfates.

Representative ion exchange techniques are disclosed in a wide variety of patents including U.S. Pat. No. 3,140,249; U.S. Pat. No. 3,140,251; and U.S. Pat. No. 3,140,253.

Following contact with the salt solution of the desired replacing cation, the zeolites are then preferably washed with water and dried at a temperature ranging from 150° F. to 1,500° F. for periods of time ranging from 1 to 48 hours or more.

Regardless of the cations replacing the sodium in the synthesized form of the ZSM-12 the spatial arrangement of the aluminum, silicon and oxygen atoms which form the basic crystal lattices of ZSM-12, remains essentially unchanged by the described replacement of sodium or other alkali metal as determined by taking an X-ray powder diffraction pattern of the ion-exchanged material. Such X-ray diffraction pattern of the ion-exchanged ZSM-12 reveals a pattern substantially the same as that set forth in Table 1 above.

The aluminosilicates prepared by the instant invention are formed in a wide variety of particular sizes. Generally speaking, the particles can be on the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the ZSM-12 with another material resistant to the temperatures and other conditions employed in organic conversion processes. Such materials include active and inactive materials and synthetic or naturally occurring zeolites as well as inorganic materials such as clays, silica and/or metal oxides. The latter may be either naturally occurring or in the form of gelatinous precipicates or gels including mixtures of silica and metal oxides. Use of a material in conjunction with the ZSM-12, i.e., combined therewith which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Normally, zeolite materials have been incorporated into naturally occurring clays, e.g., bentonite and kaolin, to improve the crush strength of the catalyst under commercial operating conditions. These materials, i.e., clays, oxides, etc., function as binders for the catalyst. It is desirable to provide a catalyst having good crush strength because in a petroleum refinery the catalyst is often subjected to rough handling, which tends to break the catalyst down into powder-like materials which cause problems in processing. These clay binders have been employed for the purpose of improving the crush strength of the catalyst.

Naturally occurring clays which can be composited with the ZSM-12 catalyst include the montmorillonite and kaolin family, which families include the subbentonites, and the kaolins commonly known as Dixie McNamee-Georgia and Florida clays or others in which the main mineral constituent is halloysite kaolinite, dickite, nacrite, or anauxite. Such clays can be used in the raw state as originally mined or initially subjected to calcination, acid treatment or chemical modification.

In addition to the foregoing materials, the ZSM-12 catalyst can be composited with a porous matrix material such as silica-alumina, silica-magnesia, silica-zirconia, silica-thoria, silica-beryllia, silica-titania as well as ternary compositions such as silica-aluminathoria, silica-alumina-zirconia, silica-alumina-magnesia and silica-magnesia-zirconia. The matrix can be in the form of a cogel. The relative proportions of finely divided crystalline aluminosilicate ZSM-12 and organic oxide gel matrix vary widely with the crystalline aluminosilicate content ranging from about 1 to 90 percent by weight and more usually, particularly when the composite is prepared in the form of beads in the range of about 2 to about 50 percent by weight of the composite.

EXAMPLES

The following examples will illustrate the invention. It is to be understood that they are merely illustrative are not to be construed as limiting the scope of the invention.

EXAMPLE 1

The ZSM-12 of this example was prepared by dissolving 1 part $NaAlO_2$ (NALCO 680) and 3.5 parts NaOH in 125 parts $H_2O$, then adding 100 parts colloidal silica sol (containing 30% $SiO_2$). The mixture was thoroughly blended, charged into a pressure vessel and held at 300° F. for 24 hours. The mixture was cooled, 20 parts $(C_2H_5)_4NBr$ was added and the mixture throughly blended and reheated to 330° F. for 8 days.

The product was washed and dried at 250° F. It was identified as 85% ZSM-12 by x-ray diffraction. The molar $SiO_2/Al_2O_3$ ration was 82.

The material was calcined in flowing $N_2$ and 3 hours at 1000° F., then ion-exchanged three times with 1 N $NH_4NO_3$ solution (10 parts solution/1 part zeolite), washed and dried at 250° F.

The $NH_4$ ZSM-12 product was finally calcined for 3 hours at 1000° F. in flowing air to yield HZSM-12.

EXAMPLE 2

The HZSM-12 catalyst of Example 1 (7.97 grams) having a $SiO_2/Al_2O_3$ ratio of 81 was charged to a 15 cc reactor and pretreated for approximately 14 hours with $H_2$ at 900° F. and 600 psig. Following the pretreatment, the reactor was cooled to 80°–90° F. and propylene was pumped over the catalyst at 0.6 WHSV (based on zeolite or total catalyst?) and 600 psig. The reactor was run without heat input so that the reactor temperature of 117° F. was maintained by the heat of reaction. Products were collected by Condensing Under Liquid Nitrogen and analyzed by Gas Chromatography. The results are presented in Table 3.

TABLE 3

OLIGOMERIZATION OF PROPYLENE OVER HZSM-12

| Conditions | |
|---|---|
| Temperature, ° F. | 117 |
| Pressure, psig | 600 |
| WHSV | 0.6 |
| Hours on Stream | 12 |
| Propylene Conversion, wt., % | 48.1 |
| Product Analysis, wt. % | |
| $C_4$–$C_5$ | 0.2 |
| $C_6^=$ | 4.0 |
| $C_7$–$C_8$ | 0.9 |
| $C_9^=$ | 51.5 |
| $C_{10}$–$C_{11}$ | 0.8 |
| $C_{12}^=$ | 24.3 |
| $C_{13}$–$C_{14}$ | 0.4 |
| $C_{15}^=$ | 11.1 |
| $C_{16}$–$C_{17}$ | — |
| $C_{18}^=$ | 4.4 |
| $C_{19}$–$C_{20}$ | — |
| $C_{21}^=$ | .9 |
| $C_{21}+$ | 1.5 |
| | 100.0 |

EXAMPLE 3

The HZSM-12 catalyst of Example 1 (4 grams) was added to 65 grams of 1-hexene (in a flask.) The mixture was heated to 150° F. and maintained under reflux. Liquid samples were taken at 4, 22 and 48 hours and analyzed by Gas Chromatography. The results are presented in Table 4.

TABLE 4

OLIGOMERIZATION OF 1-HEXENE OVER HZSM-12

| Conditions | Feedstock | | | |
|---|---|---|---|---|
| Hours on Stream | 0 | 4 | 22 | 48 |
| Temperature, °F. | — | 150 | 150 | 150 |
| Liquid Analysis, Wt. % | | | | |
| $C_6^=$ | 99.9 | 98.4 | 91.8 | 85.5 |
| $C_7$–$C_{11}$ | 0.1 | 0.2 | 0.2 | .4 |
| $C_{12}^=$ | — | 1.6 | 7.7 | 13.2 |
| $C_{18}^=$ | — | — | 0.3 | .9 |
| | 100.0 | 100.0 | 100.0 | 100.0 |

Isomer Distribution of
$C_6^=$, %

TABLE 4-continued

| OLIGOMERIZATION OF 1-HEXENE OVER HZSM-12 | | | | |
|---|---|---|---|---|
| Peak 1 | 96.7 | 91.6 | 58.2 | 21.8 |
| Peak 2 | 1.7 | 4.4 | 23.8 | 53.1 |
| Peak 3 | 1.6 | 4.0 | 18.0 | 25.1 |
| | 100.0 | 100.0 | 100.0 | 100.0 |

The results show the remarkable efficacy of the HZSM-12 in the oligomerization and isomerization of 1-hexene.

EXAMPLE 4

In this example, the oligomerization activity of the HZSM-12 of Example 1 is compared with that of five other catalysts. In each case, the catalyst was charged to a 15 cc reactor and pretreated for approximately 14 hours with $H_2$ at 900° F. and 600 psig. Following pretreatment, the reactor was cooled to 80°–90° F. and propylene was pumped over the catalyst at approximately 0.6 WHSV and 600 psig. The reactor was run without heat input; reaction temperature was maintained by the heat of reaction. The results are reported in Table 5.

TABLE 5

| OLIGOMERIZATION ACTIVITY OF VARIOUS CATALYSTS | | |
|---|---|---|
| Catalyst | Reactor Temperature, °F. | Propylene Conversion, Wt. % |
| HZSM-12 of Example 1 | 117 | 48.1 |
| H-Beta | 94 | 5.5 |
| 65% HZSM-5/ 35% $Al_2O_3$ Binder | 100 | 6.6 |
| 90% $SiO_2$/10% amorphous $Al_2O_3$ (cracking catalyst) | 93 | 5.3 |
| $Al_2O_3$ | 100 | 0 |
| 0.6% Ni-REY/35% $Al_2O_3$ Binder | 92 | 4.3 |

The results show the remarkable activity of HZSM-12 for the oligomerization of propylene at low temperatures.

EXAMPLE 5

The HZSM-12 of his example was prepared by dissolving 1 part $Al(NO_3)_3.9H_2O$, 3.8 parts NaOH and 20 parts $(C_2H_5)_4NBr$ in 280 parts $H_2O$, adding 35 parts of 40% $(C_2H_5)_4NOH$ and, finally, 65 parts of Hi-Sil (a precipitated silica containing about 90% $SiO_2$). The mixture was charged to a pressure vessel, thoroughly agitated and held at 50° C. for 24 hours, then heated to 160° C. and held at this temperature for 58 hours.

The product was washed and dried at 120° C. It was identified as 95% ZSM-12 by x-ray diffraction with the following chemical analysis:

| | | |
|---|---|---|
| $SiO_2$ | 85.3 wt % | |
| $Al_2O_3$ | 0.80 | |
| $Na_2O$ | 0.40 | |
| N | 0.92 | $SiO_2/Al_2O_3$ = 181 |
| C | n.a. | |
| Ash | 89.2 | |

The material was calcined in flowing $N_2$ for 2 hours at 550° C., followed by 2 hours in air, then ion-exchanged three times with 0.5 N $NH_4Cl$ solution (17 parts solution/1 part of zeolite) for 1 hour each at 80° C., washed and dried at 120° C.

The $NH_4ZSM$-12 product was finally calcined for 3 hours at 550° C. in flowing air to yield HZSM-12.

EXAMPLE 6

The catalyst of Example 5 (8.2 grams) was charged to a 15 cc reactor and pretreated as described in Example 2. Propylene was pumped over the catalyst at 0.6 WHSV and 600 psig. The results are presented in Table 6.

TABLE 6

| OLIGOMERIZATION OF PROPYLENE OVER HZSM-12 | | | |
|---|---|---|---|
| Conditions | | | |
| Temperature °F. | 104 | 159 | 147 |
| Pressure, psig | 600 | 600 | 600 |
| WHSV | 0.6 | 0.6 | 0.6 |
| Hours on Stream | 6 | 12 | 18 |
| Propylene Conversion, Wt. % | 61.7 | 99+ | 83.9 |
| Product Analysis, Wt. % | | | |
| $C_4$-$C_5$ | .1 | .2 | .1 |
| $C_6^=$ | .5 | 3.6 | 16.1 |
| $C_7$-$C_8$ | .1 | .1 | .8 |
| $C_9^=$ | 59.7 | 69.1 | 68.9 |
| $C_{10}$-$C_{11}$ | .3 | .4 | 1.2 |
| $C_{12}^=$ | 27.3 | 19.2 | 9.6 |
| $C_{13}$-$C_{14}$ | .1 | .1 | .9 |
| $C_{15}^=$ | 8.7 | 5.5 | 1.7 |
| $C_{16}$-$C_{17}$ | 0 | .3 | .3 |
| $C_{18}^=$ | 3.2 | 1.3 | .3 |
| $C_{19}+$ | 0 | .2 | .1 |
| | 100.0 | 100.0 | 100.0 |

EXAMPLE 7

The HZSM-12 catalyst of Example 5 (2.0 grams) was placed in an autoclave along with 25 ml of n-octane and 100 ml propylene and heated to 150° C. (302° F.) which resulted in a pressure of 780 psig. Small liquid samples were taken approximately every hour through a dip tube which extended into the reaction mixture. Liquid samples were analyzed by capillary gas chromatography using n-octane as an internal standard. The results are presented in Table 7.

TABLE 7

| OLIGOMERIZATION OF PROPYLENE OVER HZSM-12 | | | |
|---|---|---|---|
| Conditions | | | |
| Temperature, ° F. | 302 | 302 | 392 |
| Pressure, psig | 780 | 665 | 410 |
| Hours on Stream | 1.1 | 2.1 | 3.1 |
| Propylene Conversion, Wt. % | 34 | 43 | 79 |
| Product Analysis, Wt. % | | | |
| $C_6^=$ | 17.1 | 15.0 | 9.3 |
| $C_9^=$ | 53.4 | 62.6 | 58.0 |
| $C_{12}^=$ | 14.1 | 15.8 | 22.7 |
| $C_{15}^=$ | 4.1 | 5.0 | 7.5 |
| $C_{18}^=$ | 11.3 | 2.1 | 2.4 |
| | 100.0 | 100.0 | 100.0 |

EXAMPLE 8

The ZSM-12 of this Example was prepared by mixing 65 parts "Hi-Sil", 6.3 parts sodium hydroxide, 1 part $AL(NO_3)_3.9H_2O$, 40 parts tetraethylammonium bromide and 310 parts water. The reaction mixture was charged to an agitated autoclave and heated to about 320° F. under autogeneous pressure and held for about 17 hours. The mixture was then cooled to room temperature and 1.1 parts of NaALO$_2$ and 2.7 parts water were added. The mixture was reheated to about 320° F. and held for an additional 21 hours until crystallization was complete. The crystallized product was filtered and washed. X-ray diffraction analysis reported the product to be 90% ZSM-12. Chemical analysis of the crystalline product was reported as:

| | |
|---|---|
| SiO$_2$ | 95.1% wt |
| Al$_2$O$_3$ | 1.79% wt |
| Na | 0.34 |
| N | 0.98 |
| C | 7.6 |

This ZSM-12 was then mixed with Faiser Alumina, in a rate of 65 wt % zeolite and 35 wt % alumina, extruded through a 1/16" die and dried at 250° F.

The extrudate was then calcined in flowing N$_2$ for 3 hours at 1000° F. and then ion-exchanged with 1 N NH$_4$NO$_3$, washed and dried. This product was calcined for 3 hours at 1000° F. to yield a bound HZSM-12 catalyst.

EXAMPLE 9

The HZSM-12 catalyst of Example 8 (2.0 gram) was charged to a small tubular flow reactor. Propylene was pumped over the catalyst at 302° F. and 600 psig. Products were collected and analyzed by capillary gas chromatography. The results are presented in Table 8.

TABLE 8

OLIGOMERIZATION OF PROPYLENE OVER HZSM-12

| Conditions | | |
|---|---|---|
| Temperature, °F. | 302 | 302 |
| Pressure, psig | 600 | 600 |
| LHSV* | 15 | 4 |
| Hours on Stream | 4–5 | 7–23 |
| Propylene Conversion, Wt. % | 86 | 90 |
| Product Analysis, Wt. % | | |
| $C_6^=$ | 11.0 | 9.4 |
| $C_9^=$ | 37.0 | 32.2 |
| $C_{12}^=$ | 29.0 | 20.3 |
| $C_{15}^=$ | 15.3 | 19.4 |
| $C_{18}^=$ | 4.8 | 7.2 |
| $C_{21}^=$ | 2.8 | 3.5 |
| | 100.0 | 100.0 |

*LHSV based on zeolite

EXAMPLE 10

The HZSM-12 of Example 8 (2.0 gram) was charged to a small tubular flow reactor. 1 octene was charged at 392° F. and 350 psig. The conditions and results are presented in Table 9.

TABLE 9

OLIGOMERIZATION OF 1-OCTENE OVER HZSM-12

| Conditions | | |
|---|---|---|
| Temperature, °F. | 392 | 392 |
| Pressure, psig | 350 | 350 |
| WHSV* | 33 | 13 |
| Hours on Stream | .6–1.1 | 4.9–5.9 |
| Conversion, Wt. % | 53.4 | 59.9 |
| Product Analysis, Wt. % | | |
| $C_{16}^=$ | 84.0 | 88.8 |
| $C_{24}^=$ | 14.1 | 11.2 |
| $C_{32}^=$ | 1.9 | 0 |
| | 100.0 | 100.0 |

*Based on zeolite

EXAMPLE 11

The HZSM-12 of Example 8 (2.0 gram) was charged to the reactor described in Example 10. Technical grade pentene, containing 92% by weight 2-methyl-2-butene and 8% 2-pentene, was charged at 392° F. and 400 psig. The conditions and results are provided in Table 10.

TABLE 10

OLIGOMERIZATION OF PENTENE OVER ZSM-12

| Conditions | | |
|---|---|---|
| Temperature, °F. | 392 | 392 |
| Pressure, psig | 400 | 400 |
| WHSV* | 12 | 35 |
| Hours on Stream | 4 | 4.7 |
| Conversion, Wt. % | 76.9 | 67.9 |
| Product Analysis, Wt. % | | |
| $C_{10}^=$ | 92 | 94.7 |
| $C_{15}^=$ | 6.5 | 5.3 |
| $C_{20}^=$ | 1.5 | 0 |
| | 100.0 | 100.0 |

*Based on zeolite

EXAMPLE 12

The HZSM-12 of Example 8 (1.0 gram) and 100 ml of 1-decene were charged to an autoclave and heated to 302° F., which resulted in a pressure of 150 psig. The temperature was raised to 302° F. and the reaction allowed to proceed. Samples were withdrawn and analyzed by gas chromatography. The results are presented in Table 11.

TABLE 11

OLIGOMERIZATION OF 1-DECENE OVER HZSM-12

| Conditions | | | | | |
|---|---|---|---|---|---|
| Temperature, °F. | 302 | 302 | 392 | 482 | 482 |
| Pressure, psig | 150 | 150 | 160 | 210 | 210 |
| Hours on Stream | .6 | 1.6 | 2.8 | 4.2 | 5.2 |
| Conversion, Wt. % | 2.5 | 3.6 | 14.8 | 43.2 | 59.7 |
| Product Analysis, Wt. % | | | | | |
| Light Ends $C_{10}^-$ | 9.0 | 6.0 | 1.8 | 5.5 | 7.5 |
| $C_{10}$–$C_{20}$ | 31.0 | 8.0 | 3.6 | 17 | 20.5 |
| $C_{20}^=$ | 60.0 | 86.0 | 91.4 | 72 | 62.0 |
| $C_{20}^+$ | — | — | 3.2 | 6.5 | 10.0 |
| | 100.0 | 100.0 | 100.0 | 100.0 | 100.0 |

EXAMPLE 13

The HZSM-12 (2.5 gram) was charged to a small tubular flow reactor. Propylene was charged at atmospheric pressure and temperature above 500° F. The conditions and results are provided in Table 12.

TABLE 12

REACTION OF PROPYLENE OVER HZSM-12

| Conditions | | | | | |
|---|---|---|---|---|---|
| Temperature, °F. | 524 | 551 | 577 | 605 | 656 |
| Pressure | atm | atm | atm | atm | atm |
| WHSV | .5 | .5 | .5 | .5 | .5 |
| Days on Stream | 1.0 | 1.9 | 2.8 | 5.8 | 6.7 |
| Propylene Conversion, Wt. % | 74 | 71 | 69 | 69 | 65 |
| Product Analysis, Wt. % | | | | | |

TABLE 12-continued
REACTION OF PROPYLENE OVER HZSM-12

| | | | | | |
|---|---|---|---|---|---|
| $H_2$ | .3 | .1 | 0 | 0 | .1 |
| $C_1=C_2$ | .1 | .1 | 0 | 0 | .2 |
| $C_3$ Paraffin | 2.5 | 2.7 | 2.7 | 1.7 | 2.2 |
| $C_3^=$ | 25.7 | 29.4 | 31.3 | 30.7 | 35.6 |
| $i$-$C_4$ | 1.3 | 1.5 | 1.9 | 1.9 | 1.6 |
| $n$-$C_4$ | 0.3 | 6.5 | 0.4 | .1 | .7 |
| $C_4^=$ | 4.1 | 4.4 | 5.8 | 10.9 | 7.7 |
| $i$-$C_5$ | 1.2 | 1.2 | 1.4 | 1.0 | 1.1 |
| $n$-$C_5$ | 0.1 | 0 | 0 | 0 | 0 |
| $C_5^=$ | 6.4 | 7.3 | 10.0 | 10.8 | 9.8 |
| $C_6$ + Paraffin | 8.1 | 5.3 | 9.7 | 3.0 | 3.3 |
| $C_6$ + Olefin | 49.4 | 47.0 | 86.0 | 39.5 | 37.7 |
| $C_6$ + Other | .6 | .6 | .8 | .4 | .6 |
| | 100 | 100 | 100 | 100 | 100 |

The results shown in Table 12 illustrate the criticality of the low temperature liquid phase operation for the conversion of olefins to oligomer product. The products produced in the high temperature operation of Example 13 included cracked products, paraffins and light gas. In contrast, the products produced in accordance with the process of the present invention, as exemplified by Examples 2 and 6, include primarily olefin oligomer.

It will be understood that the foregoing description is merely illustrative of preferred embodiments of the invention of which many variations may be made by those skilled in the art within the scope of the following claims without departing from the spirit thereof.

I claim:

1. A process for the selective oligomerization of linear and branched chain $C_2$ to $C_{12}$ olefins which comprises contacting said olefins in the liquid phase with ZSM-12 at temperatures from about 80° F. to about 400° F.

2. The process of claim 1 wherein said contacting is carried out at a WHSV, based on zeolite, of from about 0.1 to about 10.

3. The process of claim 1 wherein a portion of the original cations associated with the zeolite are replaced by another cation.

4. The process of claim 3 wherein the replacing cation is a metal cation.

5. The process of claim 4 wherein the metal cation is nickel.

6. The process of claim 1 wherein the ZSM-12 used is in the H-form.

7. The process of claim 1 wherein the zeolite is incorporated in a matrix.

8. The process of claim 1 wherein the pressure is sufficient to maintain the system in the liquid phase.

9. The process of claim 1 wherein the olefin feed is selected from the group consisting of $C_3$ to $C_9$ linear and branched chain olefins.

10. The process of claim 1 wherein the temperature is from about 80° to about 400° F.

* * * * *